United States Patent [19]

Verbrugge et al.

[11] Patent Number: 4,812,581
[45] Date of Patent: Mar. 14, 1989

[54] CATALYTIC HYDROGENOLYSIS

[75] Inventors: Pieter A. Verbrugge; Jannetje de Waal, both of Amsterdam, Netherlands

[73] Assignee: Shell Oil Company, Houston, Tex.

[21] Appl. No.: 115,004

[22] Filed: Oct. 28, 1987

[30] Foreign Application Priority Data

Nov. 18, 1986 [GB] United Kingdom ............... 8627493

[51] Int. Cl.$^4$ .......................................... C07D 205/04
[52] U.S. Cl. .................................................. 548/953
[58] Field of Search ............................................ 548/953

[56] References Cited

U.S. PATENT DOCUMENTS

| | | | |
|---|---|---|---|
| 4,555,260 | 11/1985 | Devlin | 71/88 |
| 4,560,507 | 12/1985 | Orr | 260/239 A |
| 4,578,507 | 3/1986 | Wada et al. | 560/14 |
| 4,634,554 | 1/1987 | Wood et al. | 548/950 |
| 4,665,197 | 5/1987 | de Niesarink et al. | 548/953 |
| 4,721,793 | 1/1988 | Mason et al. | 548/953 |

FOREIGN PATENT DOCUMENTS

| | | |
|---|---|---|
| 0029265 | 5/1981 | European Pat. Off. . |
| 0125714 | 11/1984 | European Pat. Off. . |
| 0140437 | 8/1985 | European Pat. Off. . |
| 0165637 | 12/1985 | European Pat. Off. . |
| 177354 | 4/1986 | European Pat. Off. . |

*Primary Examiner*—Donald G. Daus
*Assistant Examiner*—C. Cseh

[57] ABSTRACT

Preparation of azetidine-3-carboxylic acid or a salt thereof from N-benzylazetidine-3-carboxylic acid or a salt thereof by catalytically hydrogenating the N-benzylazetidine-3-carboxylic compound in the presence of water, formate ions, and ammonium and/or alkylammonium ions. Novel ammonium and alkylammonium salts are claimed.

10 Claims, No Drawings

CATALYTIC HYDROGENOLYSIS

FIELD OF THE INVENTION

This invention relates to the catalytic hydrogenolysis of N-benzylazetidine-3-carboxylic acid or a salt thereof, a step in the preparation of azetidine-3-carboxylic acid.

BACKGROUND OF THE INVENTION

Azetidine-3-carboxylic acid is known from EP 29265 and a U.S. counterpart thereof, U.S. Pat. No. 4,555,260, as a gametocide.

A known method for preparing the compound, described in EP 125714 and corresponding U.S. Pat. No. 4,560,507, involves catalytic hydrogenolysis of N-benzylazetidine-3-carboxylic acid using molecular hydrogen in the presence of a palladium on charcoal catalyst, in methanol. However, this method cannot be used to hydrogenolyse the azetidine compound at a concentration which is economically attractive and moreover the need to supply hydrogen gas is a disadvantage. Another known method for such a reaction, described in EP 140437 and corresponding U.S. Pat. No. 4,634,554, uses acetic acid instead of methanol. However, this system has drawbacks. Firstly, after removal of the catalyst the acetic acid has to be flashed off. However, it has a high boiling point (118° C. at 76 cm Hg) and a high tenacity towards azetidine-3-carboxylic acid. After flashing off, therefore, further purification is required in order to obtain a product of acceptable purity. Secondly, acetic acid is not completely inert to azetidine-3-carboxylic acid, since some N-acetylazetidine-3-carboxylic acid is formed. The Applicants discovered that the formation of N-acetylazetidine-3-carboxylic acid could be suppressed by using an acetic acid/water (1/1 by volume) solvent system, but that a new disadvantage arose, namely that the speed of hydrogenation was reduced; and when it was attempted to reduce N-benzylazetidine-3-carboxylic acid in water alone using molecular hydrogen and palladium on charcoal as catalyst it was found that the reaction terminated prematurely, because catalyst clogged at the interface between the water and the toluene, and was thus deactivated.

It is known that catalytic hydrogenolysis of a wide range of compounds may be effected in the absence of molecular hydrogen, provided that a compound which serves as a hydrogen donor is present. In relation to the removal of protecting benzyl-type groups cyclohexane and 1,4-cyclohexadiene have been used as hydrogen donors (J. C. S. Perkin I, vol 5,490–1, 1977; J. Org. Chem., vol. 43, No. 21, p. 4194–6, 1977). N,N-dimethylbenzylamine has been reduced to toluene using triethylammonium formate as hydrogen donor but it is reported that the reaction did not appear to be very useful because it was so slow (J. Org. Chem. vol. 45, No. 24, p. 4926–9). In J. Org. Chem., vol. 44, No. 19, p. 3442–5, 1977 there is described a more advantageous method of removing benzyl and benzyloxycarbonyl protecting groups from peptide compounds, by catalytic hydrogenolysis using formic acid as hydrogen donor. For example, the N-benzyl group was removed from N(epsilon)-benzyllysine by treatment with an equal weight of palladium black in 88% formic acid and n-propanol/water, at room temperature, in 81% yield after 10 hours.

In accordance with the prior art the Applicants sought to use formic acid to replace molecular hydrogen, using amounts of catalyst more commensurate with industrial practice. However, their attempts were not successful, hydrogenolysis either not taking or taking place only in low yield.

Further experiments of the Applicants, based on the use of molecular hydrogen, had revealed an ammoniacal solvent system (methanol/ammonia) to be disadvantageous, ring-opened products being formed in substantial amounts, and proving difficult to remove.

SUMMARY OF THE INVENTION

The present invention resides in the surprising development that azetidine-3-carboxylic acid or a salt thereof may be prepared by catalytic hydrogenolysis of N-benzyl-azetidine-3-carboxylic acid or a salt thereof in the presence of water, formate ions, and ammonium and/or alkylammonium ions.

The process preferably takes place at ambient temperature, that is, about 20° C., or at a moderate temperature above ambient temperature, for example up to about 80° C. A preferred temperature range is 30° to 60° C.

Suitably at least one molar equivalent of formate ions is employed, per mole of N-benzylazetidine-3-carboxylic anion, and the molar ratio is preferably in the range 1 to 4, especially 1.1 to 3. The ammonium and/or alkylammonium ions (considered together if both are present) need not be present in identical concentration to the formate ions and the reaction may proceed efficiently when their concentration is lower than the formate ion concentration, and lower than the N-benzylazetidine-3-carboxylic anion concentration. The molar ratio of the ammonium/alkylammonium ions to N-benzylazetidine-3-carboxylic anion is preferably in the range 1 to 4, especially 1.1 to 3. Conveniently, the formate ions and the ammonium/alkylammonium ions are in substantially identical concentration.

Whilst the azetidine starting material for the process of the present invention may be a salt, such as hydrohalide, alkali metal or the like, of N-benzylazetidine-3-carboxylic acid the preferred starting material is the acid itself, there being only small amounts of metal ions, preferably substantially none, in the reaction mixture.

Preferred alkylammonium ions have 1, 2 or 3 alkyl groups, each, preferably, of up to 4 carbon atoms. The ions are suitably formed when formic acid is contacted with a primary, secondary or, preferably, a tertiary alkyl amine, especially triethylamine. The simple ammonium ion $NH_4^+$ is, however, also preferred, being cheap and convenient. It also gives advantages of easy purification on completion of the reaction: excess ammonium formate may be removed by raising the temperature sufficiently for it to be destroyed. Subsequently, when flashing off the water, it is found that the ammonium carbonate produced during the hydrogenolysis dissociates into gaseous ammonia and carbon dioxide.

An organic solvent may optionally be present but is not essential to the performance of the reaction. When an organic solvent is employed it is suitably a polar, water miscible solvent such as an alcohol, for example, methanol or ethanol or the like.

Many conventional catalysts are known to those of skill in the art for hydrogenolysis reactions to remove protecting groups from the amino functions. Suitable catalysts are listed in *Chemical Reviews*, 1985, Vol. 85, No. 2, pages 129–170. Preferred catalysts for the present invention are based on palladium, e.g., palladium hydroxide and especially palladium metal. Finely divided palladium on an inert carrier such as carbon or charcoal is particularly useful.

Whilst the amount of water used in the process of the present invention may vary considerably it is generally preferred to avoid excessive quantities of water, since excess water may have to be removed after the reaction is completed, and because the reaction proceeds more efficiently with lower quantities of water. Preferably the amount of water used in the process of the present invention is 1 to 3, more preferably 1 to 1.5 times that required to dissolve the reaction partners, and it is especially preferred that the amount of water used is just sufficient to dissolve the reaction partners. It is found that this is commonly achieved with an amount of water approximately equal in weight to N-benzylazetidine-3-carboxylic anion.

During the process according to the present invention toluene separates as an upper layer, but only towards the end of the reaction provided a relatively small amount of water is present. Moreover no clogging of catalyst at the layer separating the phases has been observed, in contrast to the earlier attempt made by the Applicants to effect the hydrogenolysis in an aqueous system. Moreover ring-opened products such as those observed in substantial amounts when the Applicants previously attempted to use an ammoniacal system, have only rarely been observed, and then only in trace amounts.

The azetidine starting material, preferably N-benzylazetidine-3-carboxylic acid, otherwise a salt thereof, may be produced in a number of ways. In one method N-benzyl-3,3-bis(hydroxymethyl)azetidine is oxidized, chemically or electrochemically, by contact with nickel in an oxidation state of at least 3, and the dicarboxylic product is then (mono)decarboxylated, for example by heating an aqueous solution thereof, preferably under acid conditions. In another preferred method N-benzyl-3,3-bis(hydroxymethyl)azetidine is treated with an alkali metal hydroxide, preferably potassium hydroxide, at a temperature in the range 175° to 225° C., in the presence of zinc and/or cadmium and/or a compound thereof. The resulting mixture is preferably then treated for the removal of alkali metal ions, to leave N-benzylazetidine-3-carboxylic acid in the presence of formic acid. The removal of the alkali metal ions may be effected in many ways. One convenient method is to treat the reaction product with tartaric or oxalic acid, to precipitate potassium bitartrate or bioxalate. Hydrogenolysis, in accordance with the invention, is then effected, advantageously with at least a portion of the formate ions required for the hydrogenolysis being those co-produced with the N-benzylazetidine-3-carboxylic acid in the reaction of the hydroxide and N-benzyl-3,3-bis(hydroxymethyl)azetidine, thus reducing the amount of formate ions required to be added for the hydrogenolysis.

The invention also relates in a further aspect, to the novel salts of formula

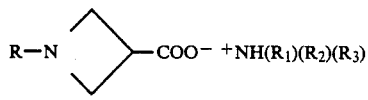

where R represents a hydrogen atom or a benzyl group and each of $R_1$, $R_2$ and $R_3$ independently represent a hydrogen atom or an alkyl group containing up to 4 carbon atoms.

EXAMPLES

The invention will now be further described by means of the following Examples which should not be regarded as limiting the invention in any way. In these Examples conversion was assessed at intervals by removing samples from the reaction mixture and taking NMR spectra thereof. Identity was assessed by NMR and/or IR spectra. Purity was assessed at the end of the reactions by hplc.

EXAMPLE 1

Preparation of azetidine-3-carboxylic acid from N-benzylazetidine-3-carboxylic acid N-benzylazetidine-3-carboxylic acid (9.5 g), 50 mmol), methanol (50 ml), water (10 ml), ammonium formate (10 g, 169 mmol) and 10% palladium on charcoal catalyst (1 g) were mixed at ambient temperature. After 10 hours at ambient temperature the conversion to azetidine-3-carboxylic acid was 60%. The temperature was raised to 35° C. After 4 hours at this temperature the conversion was 80% and after 10 hours 100%. The solution was filtered, the filtrate flashed and the residue recrystallized from isopropanol, giving 4.15 g of azetidine-3-carboxylic acid.

EXAMPLE 2

Preparation of azetidine-3-carboxylic acid from N-benzylazetidine-3-carboxylic acid N-benzylazetidine-3-carboxylic acid (50 mmol), 10% palladium on charcoal catalyst (0.5 g) and ammonium formate (55 mmol) in 25 ml water was maintained at 40°–45° C. for 6 hours. The reaction mixture was left overnight and then worked up as described in Example 1, to give 4.35 g of azetidine-3-carboxylic acid.

The above experiment was repeated using 75 mmol and 150 mmol of ammonium formate and in each case similar results were achieved.

EXAMPLE 3

Preparation of azetidine-3-carboxylic acid from N-benzylazetidine-3-carboxylic acid To a mixture of N-benzylazetidine-3-carboxylic acid (58.5 g), water (50 ml), formic acid (19.8 g) and triethylamine (16 g) (molar ratio of triethylamine to formic acid to N-benzylazetidine-3-carboxylic acid of approximately 3/10/6) was added 10.4 g of 5% palladium on charcoal/55% water catalyst (i.e. 4.7 g 5% palladium on charcoal/5.7 g water). A stormy gas evolution followed, taking about 30 minutes, and the temperature rose to 35° C. The reaction mixture was not worked up but NMR analysis indicated that the conversion to azetidine-3-carboxylic acid was 85%.

EXAMPLE 4

Preparation of azetidine-3-carboxylic acid from N-benzyl-3,3-bis(hydroxymethyl)azetidine N-Benzyl-3,3-bis(hydroxymethyl)azetidine (41.5 g), potassium hydroxide (30.05 g) and zinc oxide (2.4 g) were heated together for 2.5 hours at 200° C. The reaction mixture was quenched with 150 ml methanol containing 1.9 g of 87% phosphoric acid. The resulting mixture was filtered and to the filtrate was added tartaric acid (70.1 g) in water/methanol (100 ml, 40/60).

The pH of the solution was immediately adjusted to 6.7 with ammonia solution. The resulting mixture was filtered, to remove potassium bitartate (88.1 g). The filtrate was flashed with the residue (52 g) was taken up in water (50 ml), treated with activated charcoal, and filtered. To the resulting colourless filtrate was added ammonium formate (6.3 g) and 10% palladium on charcoal (1 g). The reaction mixture was maintained at 40° C. for 18 hours, then the temperature was raised to 70° C. and another batch of ammonium formate (6.3 g) was added. After 10 hours the conversion of N-benzylazetidine-3-carboxylic acid to azetidine-3-carboxylic acid was complete (100%). Recrystallisation from ethanol yielded 14.8 g of azetidine-3-carboxylic acid (purity, as determined by hplc analysis, 97% containing as impurity water, and inorganics: namely, 0.54 wt% K+, 0.07 wt% Na+, $Zn^{2+}$ <10 ppm).

EXAMPLE 5

Preparation of azetidine-3-carboxylic acid from N-benzyl-3,3-bis(hydroxymethyl)azetidine N-benzyl-3,3-bis(hydroxymethyl)azetidine (41.5 g), potassium hydroxide (30 g) and zinc oxide (2 g) were heated together for 2 hours at 200° C. The reaction mixture was quenched with 200 ml methanol containing 1.0 g of 87% phosphoric acid. The resulting mixture was filtered and worked up to remove inorganic by-products, leaving 55 g of residue comprising N-benzylazetidine-3-carboxylic acid. A solution in water of ammonia (700 mmol) and formic acid (500 mmol) (3 molar equivalents of ammonium formate per mole of N-benzylazetidine-3-carboxylic acid) was added to the residue. 2 g of 10% palladium on charcoal was added and the mixture heated for 10 hours at 40° C. The conversion to azetidine-3-carboxylic acid was nearly 100%. The temperature was raised to 60° C. to accelerate decomposition of remaining ammonium formate. The resulting solution was filtered and flashed and the resulting solid recrystallized from ethanol, yielding 13.2 g of azetidine-3-carboxylic acid (purity 98% by hplc; contained 0.04 wt% K+, 0.13 wt% Na+, $Zn^{2+}$ <2 ppm).

EXAMPLE 6

Preparation of azetidine-3-carboxylic acid from N-benzyl-3,3-bis(hydroxymethyl)azetidine The procedure of Example 5 was repeated, except that the hydrogenolysis of N-benzylazetidine-3-carboxylic acid was carried out using 1.1 molar equivalents of added ammonium formate, based on N-benzylazetidine-3-carboxylic acid, and the final recrystallization was effected using isopropanol. The yield of azetidine-3-carboxylic acid was 15.8 g (purity 96% by hplc; contained 1.1 wt% K+, 0.1 wt% Na+, 5 ppm $Zn^{2+}$).

EXAMPLE 7

Preparation of azetidine-3-carboxylic acid from N-benzyl-3,3-bis(hydroxymethyl)azetidine N-Benzyl-3,3-bis(hydroxymethyl)azetidine (104.5 g), potassium hydroxide (79 g) and cadmium nitrate (2.14 g) were heated together for 1 hour at 200° C. The reaction mixture was quenched with 400 ml methanol containing 1.0 g of 87% phosphoric acid. The resulting mixture was filtered and worked up to remove inorganic impurities. To the residual solution was added formic acid (47.3 g). The mixture was cooled, then 25% aqueous ammonia (75 g) and 15.5 g of 5% palladium on charcoal/55 wt% of water were added. The reaction mixture was maintained around 40° C. until gas evolution ceased (20 hours. The temperature was raised to 60° C. to remove excess ammonium formate and the solution was filtered, flashed and recrystallized from isopropanol, yielding 43 g of azetidine-3-carboxylic acid (purity 96% by hplc; contained 0.8 wt% K+, 0.13 wt% Na+, $Zn^{2+}$ <4 ppm $Cd^{2+}$ <2 ppm).

The percentage yields given in Examples 4 to 7 are of azetidine-3-carboxylic acid, calculated on N-benzyl-3,3-bis(hydroxymethyl)azetidine. The conversion of the latter compound to the intermediate, N-benzylazetidine-3-carboxylic acid was not measured but it is estimated that the hydrogenolysis and work up of the final step gave azetidine-3-carboxylic acid from N-benzylazetidine-3-carboxylic acid in at least 90% yield.

EXAMPLE 8

Preparation of azetidine-3-carboxylic acid (ACA) from N-benzyl-azetidine-3-carboxylic acid (BACA)

Further 0.25 liter scale experiments (employing 48 g of BACA), were conducted and the results are presented in tabular form below.

| BACA mol/l | HCOOH mol/l | NH₄OH mol/l | Pd/C mmol/l | T hr | t °C. | ACA YIELD % ON BACA | ACA PURITY (by hplc) |
| --- | --- | --- | --- | --- | --- | --- | --- |
| 1.0 | 3.0 | 3.0 | 11 | 2.5 | 50 | >99 | >99 |
| 1.0 | 3.0 | 3.0 | 8.5 | 3.5 | 50 | >99 | >99 |
| 1.0 | 3.0 | 3.0 | 6.5 | 5 | 50 | >99 | >99 |
| 1.0 | 3.0 | 3.0 | 4.5 | 7 | 50 | >99 | >99 |
| 1.0 | 3.0 | 3.0 | 2 | >23 | 50 | 97 | — |

Comparative Examples

EXAMPLE 9

N-Benzylazetidine-3-carboxylic acid (19.1 g) in water (15 ml), acetic acid (50 ml) and formic acid (6.9 g) were warmed to 60° C. with stirring, under a nitrogen atmosphere. 10% palladium on charcoal catalyst (1 g) was added, initiating a rapid gas evolution which ceased after about 30 minutes. Analysis revealed that very little debenzylation had taken place, whilst nearly all the formic acid had disappeared.

EXAMPLE 10

N-Benzylazetidine-3-carboxylic acid (9.6 g) and 10% palladium on charcoal catalyst (0.5 g) in formic acid (20 ml) were heated to 65° C. but there was no gas evolution, indicating that no hydrogenolysis took place. Apparently the catalyst was deactivated under these conditions, because even after cooling down and carefully neutralising with ammonia no reaction could be induced.

EXAMPLE 11

N-benzylazetidine-3-carboxylic acid (9.6 g), water (10 ml) and 1.4 g of 5% palladium on charcoal/55% water were heated to 35° C. and formic acid (3.45 g) was slowly added. Gas evolved, but analysis revealed that substantially no debenzylation had taken place.

EXAMPLE 12

To a mixture of N-benzylazetidine-3-carboxylic acid (65 g), water (65 ml) and 10 g of 5% palladium on charcoal/55% water at room temperature was slowly added formic acid (22 g). A stormy gas evolution took place and on its completion the conversion to azetidine-3-carboxylic acid was determined to be 35%.

EXAMPLE 13

N-Benzylazetidine-3-carboxylic acid (34.5 g), water (50 ml), methanol (50 ml), 25% aqueous ammonia (15 ml) and 10% palladium on charcoal catalyst (1 g) were mixed and hydrogen gas was passed through the mixture. Since no hydrogen uptake was observed at room temperature the temperature was slowly raised until, at about 70° C., hydrogen uptake was observed. Intermediate analysis indicated that reaction was extremely slow. After 2 days at 70° C. an additional 1 g of 10% palladium on charcoal catalyst was added, and after 4 days, another 0.5 g. Debenzylation was complete after 5 days and the mixture was worked up by filtering the catalyst and flashing off the solvents. NMR analysis revealed that azetidne-3-carboxylic acid was produced in contained 70% yield but that it contained ring opened products. Attempts to separate the desired product from the ring opened products, by recrystallization from isopropyl alcohol, failed.

What is claimed is:

1. A process for the preparation of azetidine-3-carboxylic acid or a salt thereof from N-benzylazetidine-3-carboxylic acid or a salt thereof, which comprises catalytically hydrogenating the N-benzylazetidine-3-carboxylic compound in the presence of water, formate ions, and ammonium and/or alkylammonium ions.

2. A process according to claim 1, wherein the hydrogenolysis is effected at a temperature in the range of about 20° C. to about 80° C.

3. A process according to claim 2, wherein the hydrogenolysis is effected at a temperature in the range of about 30° C. to about 60° C.

4. A process according to claim 1, wherein the molar ratio of formate ions to the N-benzylazetidine-3-carboxylic compound is in the range of 1 to 4.

5. A process according to claim 4, wherein the ammonium and/or alkylammonium ions are $NH_4^+$ or $(C_2H_5)_3.NH^+$.

6. A process according to claim 1, wherein the formate ions and the ammonium/alkylammonium ions are in substantially identical concentration.

7. A process according to claim 1, wherein the catalyst is a palladium catalyst.

8. A process according to claim 1, wherein the amount of water present is about 1 to 1.5 times that required to dissolve the reaction partners.

9. A process according to claim 1 wherein substantially identical amounts of $NH_4^+$ or $(C_2H_5)_3NH^+$ are present, the catalyst is a palladium catalyst and the temperature is in the range of about 30° C. to about 60° C.

10. A process for the preparation of azetidine-3-carboxylic acid from N-benzyl-3,3-bis(hydroxymethyl)azetidine, which comprises treating N-benzyl-3,3-bis(hydroxymethyl)azetidine with an alkali metal hydroxide at a temperature in the range 175° C. to 225° C. in the presence of zinc and/or cadmium and/or a compound thereof to produce the alkali metal salt of N-benzylazetidine-3-carboxylic acid, and effecting hydrogenolysis of the N-benzylazetidine-3-carboxylic anion, as claimed in claim 1, at least a portion of the formate ions required for the hydrogenolysis being co-produced with the N-benzylazetidine-3-carboxylic acid salt in the reaction from N-benzyl-3,3-bis(hydroxymethyl)azetidine.

* * * * *